(12) United States Patent
Zhao et al.

(10) Patent No.: US 9,410,880 B2
(45) Date of Patent: Aug. 9, 2016

(54) LASER DIFFERENTIAL CONFOCAL MAPPING-SPECTRUM MICROSCOPIC IMAGING METHOD AND DEVICE

(71) Applicant: BEIJING INSTITUTE OF TECHNOLOGY, Beijing (CN)

(72) Inventors: Weiqian Zhao, Beijing (CN); Han Cui, Beijing (CN); Lirong Qiu, Beijing (CN); Yun Wang, Beijing (CN)

(73) Assignee: BEIJING INSTITUTE OF TECHNOLOGY, Beijing (CN)

( * ) Notice: Subject to any disclaimer, the term of this patent is extended or adjusted under 35 U.S.C. 154(b) by 99 days.

(21) Appl. No.: 14/366,266

(22) PCT Filed: Aug. 8, 2013

(86) PCT No.: PCT/CN2013/081066
§ 371 (c)(1),
(2) Date: Jun. 18, 2014

(87) PCT Pub. No.: WO2014/110900
PCT Pub. Date: Jul. 24, 2014

(65) Prior Publication Data
US 2015/0346101 A1  Dec. 3, 2015

(30) Foreign Application Priority Data

Jan. 21, 2013 (CN) .......................... 2013 1 0026356

(51) Int. Cl.
G01N 21/00 (2006.01)
G01N 21/47 (2006.01)
G01N 21/65 (2006.01)

(52) U.S. Cl.
CPC ................ *G01N 21/47* (2013.01); *G01N 21/65* (2013.01); *G01N 21/658* (2013.01); *G01N 2201/063* (2013.01)

(58) Field of Classification Search
CPC ..... G01N 21/65; G01N 2201/063; G01J 3/44; G01J 3/0208; G01J 3/0237
See application file for complete search history.

(56) References Cited

U.S. PATENT DOCUMENTS

| 7,595,873 B1 | 9/2009 | Deck | |
|---|---|---|---|
| 2006/0012871 A1* | 1/2006 | Funk | G01J 3/02 359/385 |

(Continued)

FOREIGN PATENT DOCUMENTS

| CN | 1448707 A | 10/2003 |
|---|---|---|
| CN | 1759307 A | 4/2006 |

(Continued)

OTHER PUBLICATIONS

Kimberley F et al: "Description and Theory of a Fiber-Optic Confocal and Super-Focal Raman Microspectrometer", 1996.

(Continued)

*Primary Examiner* — Kara E Geisel
*Assistant Examiner* — Maurice Smith
(74) *Attorney, Agent, or Firm* — Gokalp Bayramoglu

(57) ABSTRACT

The present invention belongs to a technical field of optical microscopic imaging and spectral measurement, and discloses a laser differential confocal mapping-spectrum microscopic imaging method and device. The core concept of the present invention is to combine the differential confocal detection and the spectrum detection techniques and use a dichroic beam splitting system (13) to separate the Rayleigh light for geometric position detection from the Raman scattering light for spectrum detection, by mean of the property that the zero-cross point of the differential confocal curve (43) accurately corresponds to the focus of the objective, the spectral information at focus of the excitation spot being accurately captured by the zero trigger to accomplish the spectrum detection with high spatial resolution. Therefore, the present invention provides a method and device that may be able to accomplish the spectrum detection with high spatial resolution to a micro-area of a sample.

16 Claims, 7 Drawing Sheets

(56) References Cited

U.S. PATENT DOCUMENTS

| | | | |
|---|---|---|---|
| 2010/0020312 A1 | 1/2010 | Jeong et al. | |
| 2013/0162990 A1* | 6/2013 | Kobayashi | G01J 3/021 356/301 |
| 2013/0271760 A1* | 10/2013 | Froigneux | G01J 3/02 356/301 |

FOREIGN PATENT DOCUMENTS

| | | | | |
|---|---|---|---|---|
| CN | 101290293 | A | | 10/2008 |
| CN | 101526477 | A | | 9/2009 |
| CN | 101526477 | A | * | 9/2009 ............ G01N 21/65 |
| CN | 101852594 | A | | 10/2010 |
| CN | 102608098 | A | | 7/2012 |
| CN | 103091299 | A | | 5/2013 |
| CN | 103105231 | A | | 5/2013 |

OTHER PUBLICATIONS

E Kenwood Blvd et al: "Very efficient fluorescent background suppression in confocal Raman microscopy Department of Physics", 2007.

N.Everall et al: "The Influence of Out-of-Focus Sample Regions on the Surface Specificity of Confocal Raman Microscopy", 2008.

M. J. Pelletier and Neil J. Everall et al: "Control of the Out-of-Focus Light Intensity in Confocal Raman microscopy using optical preprocessing", 2009.

Jiubin Tang: "Miniature differential confocal self-focusing light focusing detection system", Acta Optics Sinica, Feb. 28, 2003, pp. 202-206.

\* cited by examiner

LASER DIFFERENTIAL CONFOCAL MAPPING-SPECTRUM MICROSCOPIC IMAGING METHOD AND DEVICE

TECHNICAL FIELD

The invention belongs to a technical field of optical microscopic imaging and spectral measurement, and relates to a laser differential confocal mapping-spectrum microscopic imaging method and device, which may be used for three-dimensional morphology reconstitution and micro-area spectrum detection for varied samples.

BACKGROUND ART

In 1990, G. J. Puppels et al., reported their invention of laser confocal Raman microscopy technology in the journal Nature, which combined Raman spectrum detection technology and laser confocal microscopy technology, and which was a revolutionary breakthrough in Raman technology. This technology not only came into the high resolution chromatography imaging characteristics of confocal microscopy, but also could perform spectral analysis to samples; which can implement chromatography detection with high resolution for the micro-area spectrum of the sample. These remarkable advantages make the laser confocal Raman microscopy technology out of common in the field of spectral measurement and rapidly develop into an important means of structure and composition analysis of sample. The laser confocal Raman microscopy technology can be widely used in the forward basic research of many disciplines, such as chemistry, biology, medicine, physics, geology, collection of evidences, forensic science and etc.

Currently, the principle of a typical laser confocal Raman microscopy is shown in FIG. 2. After sequentially passing through a first converging lens, a first pinhole, an eighth converging lens, a first beam splitting system, a quarter wave plate and an objective lens along the light path, the laser focuses on a measured sample and excites the Raman scattering light carrying the spectral characteristics of the sample; the sample is moved, in such a manner that the Raman scattering light corresponding to different parts of the tested sample passes through the quarter wave plate again and is reflected by the first beam splitting system, and then through a fourth converging lens, a fourth pinhole and a fifth converging lens, focuses into a first spectrometer to detect spectrum.

The rapid development of modern science and technology has come up with an improved requirement to the detection capacities of the micro-area spectrum and the spatial resolution; if the spatial resolution is desired to be improved, the system should be focalized accurately. In optical detection system, the measuring converging spot has a minimum size and a strongest intensity of excitation light when it is in focus. Therefore, in order to achieve high spatial resolution, it is required to capture the spectrum at a point having the strongest intensity of excitation light, thus obtaining the best spatial resolution and the optimal spectrum detection capacity. As shown in FIG. 1, all within BB' zone (a zone in which slope difference in respect to zero-cross point is not more than 10%) in the vicinity of the focus O, the existing confocal microscopy can excite the Raman spectrum of the sample and can be detected by spectrum detection system behind the pinhole. Therefore, the actual detection position of the confocal Raman microscopy is usually placed in out-of-focus BA and A'B' zones in confocal curve, causing the size of actually detected "micro-area" to be much greater than that of the focus O. Meanwhile, the signal noise ratio of confocal positioning of the utilization of Raman spectrum technology is low. The energy of the Raman spectrum may be further reduced due to the blocking effect of the pinhole; on the other hand, the expansion of the pinhole size for increasing the passing through rate of the spectrum may increase FWHM (full width at half maximum) of confocal axial intensity curve and reduce its positioning accuracy. The size of confocal pinhole in the existing confocal Raman system usually ranges from 150 μm to 200 μm. The relatively large size of pinhole also can't act well on focusing. Above reasons restrict the ability of the confocal Raman microscopy system to detect the micro-area spectrum, constraining its application to a more precise micro-area spectral measurement and analysis area. Therefore, the improvement of focalization precision of the system is the key to improve the spatial resolution.

Kimberley F et al., in "Description and Theory of a Fiber-Optic Confocal and Super-Focal Raman Microspectrometer" in 1996, proposed a method of replacing the pinhole of confocal Raman microscopy with fibre bundle to implement a non-mechanical adjustment of "pinhole" size, in which the spectral resolution of the system does not reduce when the "pinhole" size is increased; E Kenwood Blvd et al., in "Very efficient fluorescent background suppression in confocal Raman microscopy Department of Physics" in 2007, proposed that the fluorescence background of the measured sample could be reduced by about 3 orders of magnitude by combining a picosecond laser of 3-4 ps with the corresponding instantaneous exposure technology, improving the resolution of confocal Raman microscopy; N. Everall et al., in "The Influence of Out-of-Focus Sample Regions on the Surface Specificity of Confocal Raman Microscopy" in 2008, pointed out that a higher axial resolution and signal-to-noise ratio than traditional Confocal Raman spectrometer could be obtained by using an oil-immersion objective with a high numerical aperture (NA=1.4), but this method needs to prepare a sheet for the sample and can't achieve non-contact and non-destructive measurement, thereby restricting the application range of the system; M. J. Pelletier and Neil j. Everall et al., in "Control of the Out-of-Focus Light Intensity in Confocal Raman microscopy using optical preprocessing" in 2009, proposed that an interference of the Raman scattering spectrum intensity at the out-of-focus position could be eliminated by using structure pupil mask or correcting lens, thereby improving the efficiency of the spectrum detection and greatly reducing the influence of the out-of-focus area Raman spectrum in the confocal Raman system on its effective depth resolution.

The above research mainly concentrated on light source system, spectrum detection system, focusing objective system, spectral information processing, etc., which are involved in the confocal Raman microscopy system. While the overall performance of spectrum system could be improved, the spatial resolution of confocal Raman spectroscopy system has not been improved significantly. Therefore, the improvement of the spatial resolution of Raman spectrum system is still a pending issue.

In many research fields such as physical chemistry, biological medicine, film and drug, some further information of the sample could often be obtained in the form of image at the time of analyzing the chemical composition, spatial distribution and physical and chemical properties of the surface of the sample. Thus, there is a requirement to extend Raman spectrum detection from a single point analysis way to the detection and analysis of the sample within a certain area, namely the Raman spectral imaging. However, in order to obtain more accurate and more abundant measurement information, the Raman spectral imaging not only performs multiple-point Raman spectrum detection to the sample, but also needs a relative long time Raman spectrum detection to each point of the multiple-point. As a result, the Raman spectral imaging needs a relative long time for detection. It often takes a few hours to complete imaging. However, in the long-time imaging process, the instrument may be significantly influenced by, for example, environment temperature, vibration, air fluctuation, which may easily cause the instrument system to drift, thereby resulting in the out-of-focus of the detected position of the sample; since the existing confocal Raman spectroscopy does not have the ability of a real-time focus-tracking, the out-of-focus error of the sample which is caused by the offset of detected position can not be compensated, thereby restricting the improvement of the spatial resolution of the confocal Raman spectral imaging technology.

The confocal Raman spectroscopy has varied requirements for the size of detecting converging spot according to the research fields such as the detection of drug, gemstone identification, oil and gas exploration, chemical analysis and archaeology. However, the existing confocal Raman detection technology could not accurately control the size of the converging spot. As a result, the application of the confocal Raman spectral imaging technology in various fields may be constrained.

In the existing confocal Raman spectrometer, the Raman scattering light included in the scattering light of the sample collected by the system is extremely weak, which is only as much as $10^{-3}$-$10^{-6}$ times the Rayleigh light included in the scattering light of the sample collected by the system. Therefore, how to make use of the Rayleigh light in the confocal Raman spectrum detection, which is abandoned in the existing spectrum detection system and which is $10^3$-$10^6$ times stronger than the Raman scattering light, to assist the detection is a new approach to improve the spatial resolution of confocal Raman spectroscopy.

On the basis of the above situation, the present invention provides a differential confocal detection system utilizing the Rayleigh light, which is abandoned in the scattering light of the sample collected by the existing confocal Raman spectrum detection system and which is $10^3$-$10^6$ times stronger than the Raman scattering light of the sample, to perform highly precise detection. The differential confocal detection system may be combined with the spectrum detection system to synchronously detect the spatial position and spectral information. Therefore, it is desirable to achieve a "mapping & spectrum in one" differential confocal spectral imaging and detection with high spatial resolution and controllable size of measuring converging spot. The achievement of spectrum detection with high spatial resolution is one problem to be solved in the spectral microscopic test field and is of great theoretical and academic value.

The main concept of the present invention is: combining the laser differential confocal technology and spectrum detection technology, the differential confocal system using the Rayleigh light in the scattering light of the sample collected by the system to real-time focus-tracking and detect spatial position, the spectrum detection system using the Raman scattering light in the scattering light of the sample collected by the system to perform spectrum detection, and then fusing the signals of the differential confocal detection system and the Raman spectrum detection system, thereby accomplishing the focus-tracking detection and spot size controllable detection of the laser differential confocal Raman spectroscopy system, namely accomplishing the Raman spectrum detection with high spatial resolution.

SUMMARY OF THE INVENTION

One of the objects of the present invention is to overcome the shortage that the existing confocal Raman spectroscopy has difficulty in improving the spatial resolution, and to provide a laser differential confocal mapping-spectrum microscopic chromatography imaging method and device with high spatial resolution.

The laser differential confocal mapping-spectrum microscopic imaging method provided according to the present invention may comprise:

a) after passing through a first beam splitting system (8) and an objective (10), excitation beam generated by an excitation beam generation system (1) being focused on a measured sample (11) and excited Rayleigh light and Raman scattering light that carries the spectral characteristics of the measured sample (11), the excited Raman scattering light and the Rayleigh light being recycled into the light path by a system and then be reflected to a dichroic beam splitting system (13) by a first beam splitting system (8) after passing through the objective (10), after being split by the dichroic beam splitting system (13), the Raman scattering light and the Rayleigh light being separated from each other, the Rayleigh light being reflected into a differential confocal detection system (14), while the Raman scattering light being transmit into a spectrum detection system (22), and based on the property that the zero-cross point of the differential confocal curve (43) accurately corresponds to the focus of the objective, spectral information at the focus of the excitation spot being accurately captured by zero trigger to accomplish spectrum detection with high spatial resolution;

b) when a differential subtraction process is made only to the signal of the received Rayleigh light, the system performing a three-dimensional chromatography imaging with high spatial resolution; when a process is made only to the spectrum signal of the received Raman scattering light, the system performing a spectrum detection; when a process is made to the signals of both the received Rayleigh light and the Raman scattering light, the system performing a micro-area mapping-spectrum chromatography imaging with high spatial resolution that is a "mapping & spectrum in one" with high spatial resolution of geometric position information and spectral information of the measured sample;

c) the zero-cross point of the differential confocal curve (43) accurately corresponding to the focus O of the objective (10), so that in the measurement process, the measured sample (11) being accurately and real-time focus-tracking to ensure the measured sample (11) to always be focused during the whole measurement process, thereby restraining the influence of the factors such as environment temperature and vibration on the spectral measurement so as to improve the accuracy of measurement;

d) the zero-cross point of the differential confocal curve (43) corresponding to the focus O of the measurement objective (10) at which the converging spot and detection area have the smallest size, other position in linear section BB' corresponding to the out-of-focus area of the objective (10), and the size of the converging spot in front of or behind the focus within the section BB' increases as the out-of-focus amount increases; in such a manner that the size of the converging spot may be controlled by adjusting z-axial out-of-focus amount of the sample and according to the requirement of actual measurement accuracy, thus allowing the size of the detection area of the sample to be controllable.

Preferably, the excitation beam is a polarized beam that may be linearly polarized light, circularly polarized light or radially polarized light, or the excitation beam is structural beam generated by the pupil filter process, so that when used with the pupil filtering process, it may compress the size of the measuring converging spot to improve the lateral resolution of the system.

Preferably, the system may further be used to detect the scattering spectrum, wherein the scattering spectrum includes the scattering spectrums of detection fluorescence, brillouin scattering light and Compton scattering light.

The present invention also provides a laser differential confocal mapping-spectrum microscopic imaging device, comprising: an excitation beam generation system (1), a first beam splitting system (8), an objective (10), a 3D scanning stage (12), a dichroic beam splitting system (13), a spectrum detection system (22), a differential confocal detection system (14) and a data processing module (34);

wherein the first beam splitting system (8), the objective (10) and the 3D scanning stage (12) are sequentially placed in the emission direction of the excitation beam generation system (1), the dichroic beam splitting system (13) is positioned in the reflection direction of the first beam splitting system (8), the spectrum detection system (22) is positioned in the transmission direction of the dichroic beam splitting system (13), the differential confocal detection system (14) is positioned in the reflection direction of the dichroic beam splitting system (13), and the data processing module (34) is connected to the spectrum detection system (22) and the differential confocal detection system (14);

or, the excitation beam generation system (1) is placed in the reflection direction of the first beam splitting system (8), the dichroic beam splitting system (13) is sequentially placed in the transmission direction of the first beam splitting system (8) along the light path, the spectrum detection system (22) is positioned in the transmission direction of the dichroic beam splitting system (13), the differential confocal detection system (14) is positioned in the reflection direction of the dichroic beam splitting system (13), the data processing module (34) is connected to the differential confocal detection system (14) and the spectrum detection system (22); the data processing module (34) is configured to fuse and process the data acquired by the spectrum detection system (22) and the differential confocal detection system (14).

Preferably, the spectrum detection system (22) is a general spectrum detection system, which includes, sequentially placed along the light path, a seventh converging lens (46), a second spectrometer (47) positioned at the focus of the seventh converging lens (46) and a fifth detector (48) positioned behind the second spectrometer (47), wherein the general spectrum detection system is configured to perform spectrum detection of a surface layer of the measured sample;

or, the spectrum detection system (22) is a confocal spectrum detection system, which includes, sequentially placed along the light path, a fourth converging lens (23), a fourth pinhole (24) positioned at the focus of the fourth converging lens (23), a fifth converging lens (25) positioned behind the fourth pinhole (24), a first spectrometer (26) positioned at the focus of the fifth converging lens (25) and a third detector (33) positioned behind the first spectrometer (26), wherein the confocal spectrum detection system is configured to improve signal noise ratio and spatial resolution of the system and to perform spectrum chromatography detection of the measured sample.

Preferably, the excitation beam generation system (1) further includes a polarization modulator (6) and a pupil filter (7), wherein the polarization modulator (6) is configured to generate polarized light, and the pupil filter (7) is configured to generate structural beam.

Preferably, the pupil filter (7) configured to compress the excitation spot is placed between the polarization modulator (6) and the first beam splitting system (8), or is placed between the first beam splitting system (8) and the objective (10).

Preferably, the device further includes a fourth beam splitting system (40) and a microscopic observation system (37) positioned in the reflection direction of the fourth beam splitting system (40), wherein the microscopic observation system (37) is configured to observe the measured sample; wherein the fourth beam splitting system (40) is positioned between the excitation beam generation system (1) and the first beam splitting system (8) or is positioned between the first beam splitting system (8) and the objective (10).

Preferably, the data processing module (34) includes a differential subtraction module (35) configured to process the position information, and a data fusion module (36) configured to fuse the position information and the spectral information.

The present invention also provides a laser differential confocal mapping-spectrum microscopic imaging method, comprising:

A) during the lateral scanning of the measured sample (11), real-timely aiming to each of determined scanning points, a focus of an objective (10) being accurately tracked utilizing a set of axially detected differential confocal intensity response signals; after the focalization, based on the property that the zero-cross point of the differential confocal curve (43) accurately corresponds to the focus of the objective, the spectral information at the focus of the excitation spot being accurately captured by the zero trigger;

wherein the differential confocal signal and the spectral information are obtained by the following steps:

an excitation beam generation system (1) generating excitation beam, after passing through a first beam splitting system (8) and an objective (10) placed sequentially, the excitation beam focusing on the measured sample (11) and exciting Rayleigh light and Raman scattering light that carries the spectral characteristics of the measured sample (11); the Rayleigh light and the Raman scattering light being recycled into the light path by a system, following the passage of the objective (10) and the first beam splitting system (8), then entering a dichroic beam splitting system (13) to split the light, the Rayleigh light being reflected into a differential confocal detection system (14) and the differential confocal intensity response signal carrying geometric position information of the measured sample (11) being obtained via the differential confocal detection system (14), while the Raman scattering light being transmitted into a spectrum detection system (22) and the spectrum signals carrying the spectral characteristics of the measured sample (11) being obtained via the spectrum detection system (22);

B) after each of the scanning points in the lateral direction of the measured sample (11) being real-time focus-tracked according to the above steps and then spectrum signals of the scanning points being accurately captured, a set of differential confocal signals carrying the geometric position information of the measured sample (11) and spectrum signals carrying the spectral characteristics of the measured sample (11) being obtained, the signals being transmitted to a data processing module (34) to be processed; wherein the processing includes: when the differential confocal signals being only processed, the system performs a three-dimensional chromatography imaging with high spatial resolution; and/or when the spectrum signals being only processed, the system performs a spectrum detection; and/or when both the differential confocal signals and the spectrum signals are processed, the system performs a micro-area mapping-spectrum chromatography imaging with high spatial resolution, wherein the micro-area mapping-spectrum chromatography imaging is a "mapping & spectrum in one" with high spatial resolution in which the geometric position information and spectral information of the measured sample are detected simultaneously; wherein during the accurate capture of the spectrum signals, the method further includes: by mean of the differential confocal curve (43), the size of the converging spot being controlled by adjusting the axial out-of-focus amount of the sample and according to the requirement of actual measurement accuracy.

Preferably, the step of, real-time aiming to each of determined scanning points, the focus of the objective (10) is real-time tracked utilizing a set of axially detected differential confocal intensity response signals, may further comprise:

A1) axial scanning being performed at lateral planar positions where the scanning points are located to obtain a set of differential confocal intensity response signals, then the differential confocal intensity response signals being transmitted to the data processing system (34), the data processing system (34) fitting the differential confocal intensity response signals into the differential confocal curve (43), and the focus of the objective (10) being determined according to the differential confocal curve (43).

Preferably, the step of, after the focalization, based on the property that the zero-cross point of the differential confocal curve (43) accurately corresponding to the focus of the objective, the spectral information at the focus of the excitation spot being accurately captured by the zero trigger, may further comprise:

A2) the objective (10) and/or the measured sample (11) being axially moved according to the focus of the focalized objective (10), to make the measured sample (11) be positioned at the focus of the objective (10);

A3) the Raman scattering light of the measured sample (11) in focus being captured and recycled into the light path, and the spectrum signal that carries the spectral characteristics of the measured sample (11) being obtained by the spectrum detection system (22).

Preferably, the step of, by mean of the differential confocal curve, the size of the converging spot being controlled by adjusting the axial out-of-focus amount of the sample and according to the requirement of actual measurement accuracy, may include:

according to such a characteristic that the non-focal position in the linear section BB' of the differential confocal curve (43) corresponds to the out-of-focus area of the objective (10) and the size of the converging spot in front of or behind the focus within the section BB' increases as the out-of-focus amount increases, by mean of the differential confocal curve, the size of the converging spot being controlled by adjusting the axial out-of-focus amount of the sample and according to the requirement of actual measurement accuracy, thus allowing the size of the detection area of the sample to be controllable.

Preferably, the excitation beam is a polarized beam, wherein the type of polarized beam comprises: linearly polarized light, circularly polarized light or radially polarized light; or the excitation beam is structural beam generated by the pupil filtering process, wherein the structural beam generated by the pupil filtering process is used to compress the size of the measuring converging spot to improve the lateral resolution of the system.

Preferably, the method further is able to detect the scattering spectrum, wherein the scattering spectrum includes the scattering spectrums of fluorescence, brillouin scattering light and Compton scattering light.

The present invention has the following beneficial effects.

In comparison with the prior art, the present invention has the following main innovation points:

1. Based on the property that the zero-cross point of the differential confocal curve accurately corresponds to the focus of the objective, the spectral information of the excitation spot in focus may be accurately captured by the zero trigger, thereby accomplishing the spectrum detection with high spatial resolution.

2. A dichroic beam splitting system may be used to separate the Rayleigh light from the Raman scattering light carrying the information of the measured sample, wherein the Rayleigh light enters a differential confocal detection system and the Raman scattering light enters a Raman spectrum detection system, so as to realize the full utilization of light energy and make the weak Raman scattering light enter the Raman spectrum detection system to improve the spectrum detection sensitivity of the system, thereby accomplishing a "mapping & spectrum in one" with high spatial resolution of the geometric position information and spectral information of the sample.

3. The differential confocal technology may be used to accurately position the measuring converging spot and real-time track focus, so as to eliminate the environmental influence such as temperature and vibration, realize regulation and make the detection of the Raman system always accurately correspond to sample spectrum in a minimum area of excitation converging spot, thereby significantly improve the detection abilities to micro-area spectrum and geometric position of the existing confocal Raman microscopy, namely accomplishing high spatial resolution.

4. The characteristic that the linear section of differential confocal response curve corresponds to different sizes of the converging spot may be used to accurately adjust the position of converging spot, and then control the size of measuring converging spot, thereby facilitating the testing and analysis of samples having different testing requirements, namely accomplishing an adjustable size of measuring converging spot.

5. The differential confocal microscopy and the Raman spectral imaging system are combined in structure and function, so as not only to realize the chromatography imaging of geometric parameters of the sample micro-area, but also to realize the spectrum detection of the sample micro-area, namely, at the same time realize three imaging modes of the micro-scale chromatography imaging, mapping-spectrum chromatography imaging and spectral test, and significantly improve the anti-interference ability, linear and out-of-focus characteristic of imaging testing system.

In comparison with the prior art, the present invention has the following main advantages:

1) By combining the differential confocal technology and spectrum detection technology and using the precise positioning of the differential confocal system to the focus, the spatial resolution of spectrum detection may be greatly improved.

2) By using the out-of-focus area of the differential confocal response curve to regulate the size of converging spot, various test requirements may be satisfied so that the system may be of universality.

3) The differential confocal zero trigger detection technology can significantly inhibit the influence of, for example, the non-linear of the system, the reflectance of sample and the sloped surface on the measured results, facilitating to accomplish the micro structure with high resolution, high anti-interference ability and measurement with high precision and high chromatography capacity, etc.

List of reference number is as follows: 1—excitation beam generation system, 2—laser, 3—first converging lens, 4—first pinhole, 5—eighth converging lens, 6—polarization modulator, 7—pupil filter, 8—first beam splitting system, 9—¼ wave plate, 10—objective, 11—measured sample, 12—3D scanning stage, 13—dichroic beam splitting system, 14—differential confocal detection system, 15—second beam splitting system, 16—second converging lens, 17—second pinhole, 18—first detector, 19—third converging lens, 20—third pinhole, 21—second detector, 22—spectrum detection system, 23—fourth converging lens, 24—fourth pinhole, 25—fifth converging lens, 26—first spectrometer, 27—incident slit, 28—planar reflector, 29—first concave reflective converging lens, 30—spectrum grating, 31—second concave reflective converging lens, 32—exit slit, 33—third detector, 34—data processing module, 35—differential subtraction module, 36—data fusion module, 37—microscopic observation system, 38—kohler illumination system, 39—third beam splitting system, 40—fourth beam splitting system, 41—sixth converging lens, 42—fourth detector, 43—differential confocal curve, 44—confocal Raman curve, 45—confocal curve, 46—seventh converging lens, 47—second spectrometer, 48—fifth detector.

DETAILED DESCRIPTION OF THE EMBODIMENTS

The present invention will be further described with reference to the drawings and embodiments hereinafter.

The main concept of the present invention is to utilize the combination of the differential confocal detection and spectrum detection to achieve a "mapping & spectrum in one" spectrum detection.

Figure 1:
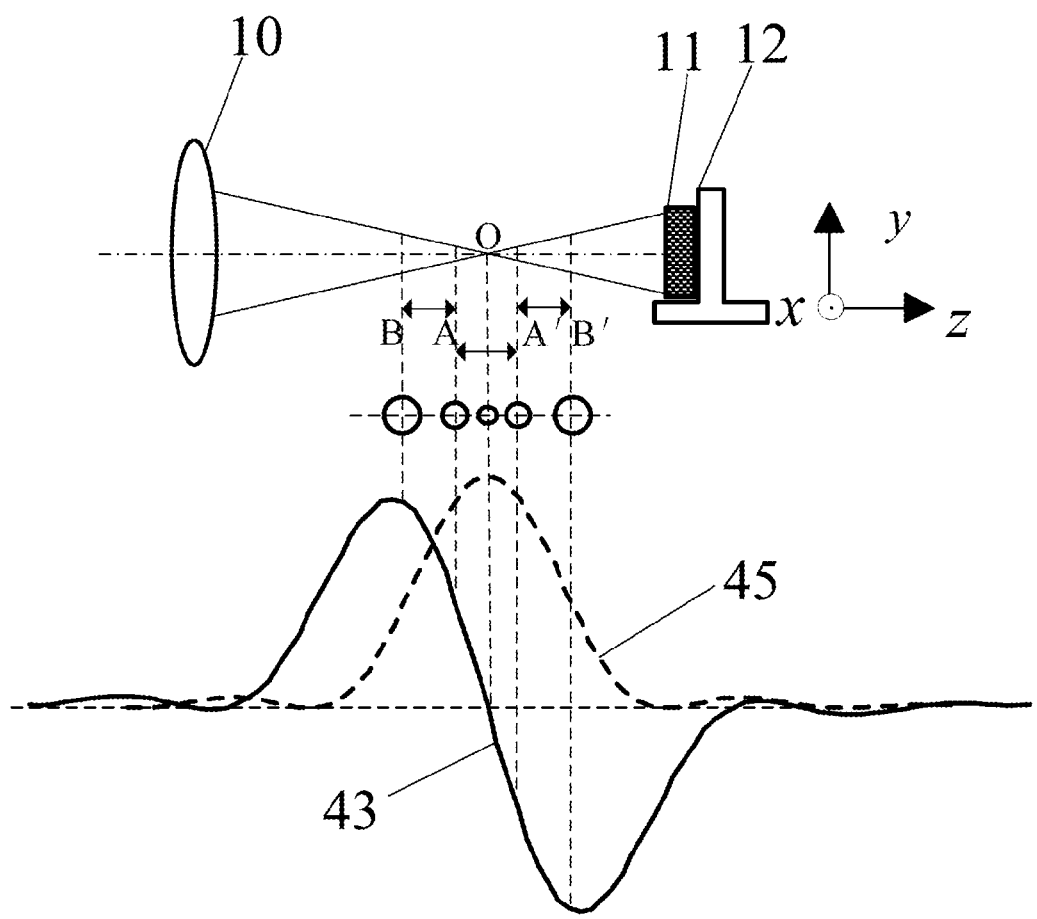
FIG. 1 is a schematic diagram of differential confocal and confocal axial response.
Figure 2:
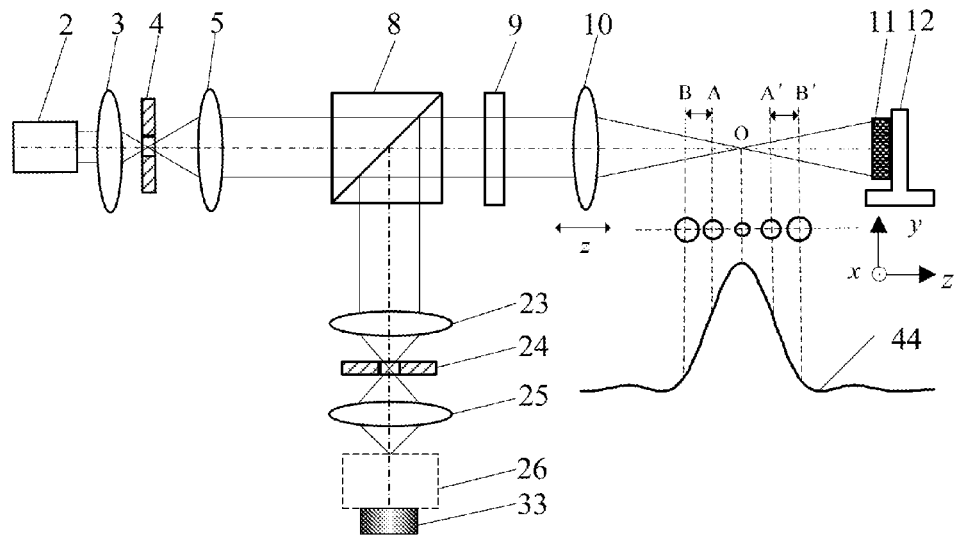
FIG. 2 is a schematic diagram of a method of the confocal Raman spectral imaging.
Figure 3:
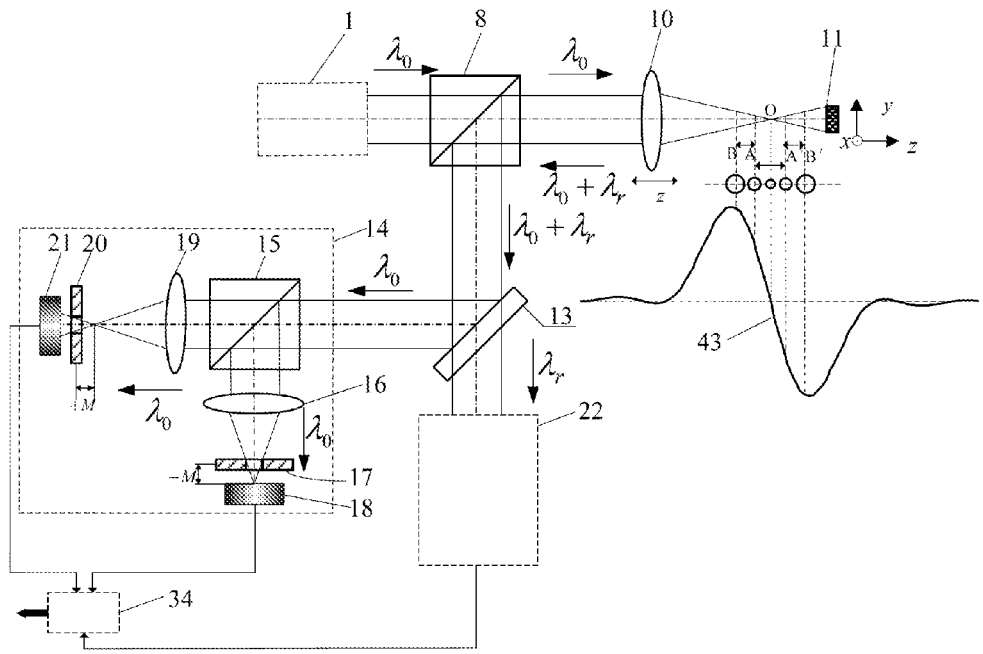
FIG. 3 is a schematic diagram of a method of laser differential confocal mapping-spectrum microscopic imaging.

As shown in FIG. 3, after passing through a first beam splitting system 8 and an objective 10, the excitation light generated by an excitation beam generation system 1 may be focused on a measured sample 11 and excited Rayleigh light and Raman scattering light that carries the spectral characteristics of the measured sample 11. The excited Raman scattering light and the Rayleigh light may be recycled into the light path by the system and then be reflected to a dichroic beam splitting system 13 by a first beam splitting system 8 following passing through the objective 10. After being split by the dichroic beam splitting system 13, the Raman scattering light and the Rayleigh light may be separated from each other. The Rayleigh light may be reflected into a differential confocal detection system 14 to perform position detection, while the Raman scattering light may be transmitted into a spectrum detection system 22 to perform spectrum detection.

Figure 4:
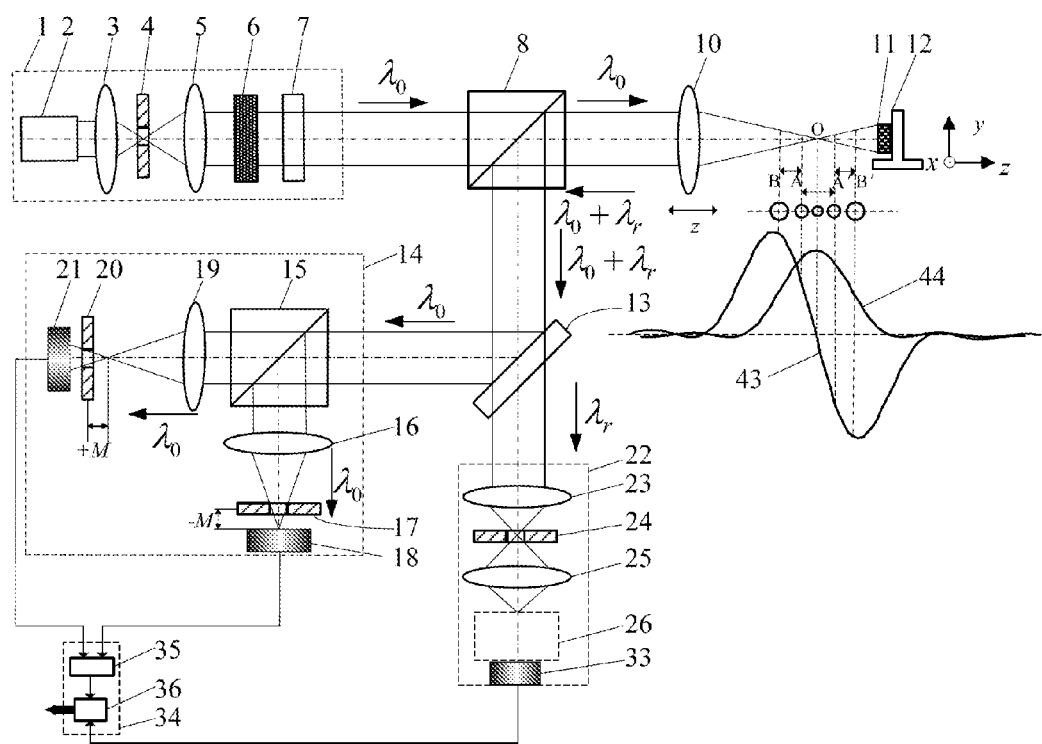
FIG. 4 is a schematic diagram of a device of laser differential confocal mapping-spectrum microscopic imaging.

As shown in FIG. 4, a laser differential confocal mapping-spectrum microscopic imaging device may include, along the light path in sequence, the excitation beam generation system 1, the first beam splitting system 8, the objective 10, the measured sample 11, a 3D scanning stage 12, the dichroic beam splitting system 13 positioned in the reflection direction of the first beam splitting system 8, the spectrum detection system 22 positioned in the transmission direction of the dichroic beam splitting system 13, and the differential confocal detection system 14 positioned in the reflection direction of the dichroic beam splitting system 13. The device may further include a data processing module 34 which combines the spectrum detection system 22 and the differential confocal detection system 14.

Figure 5:
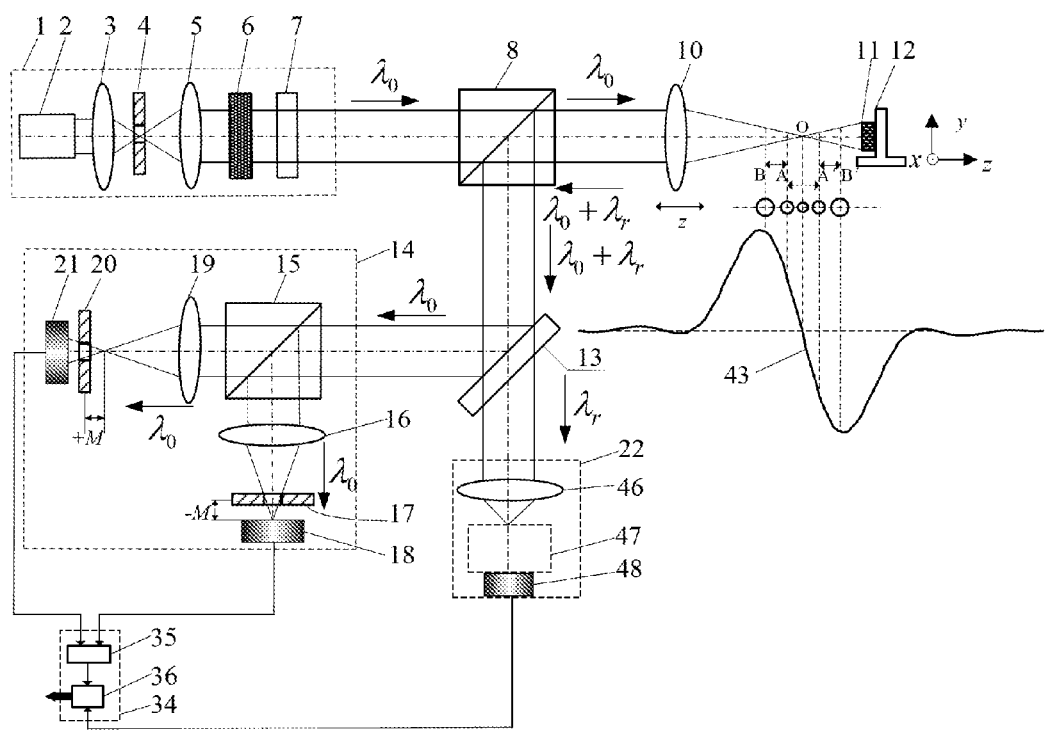
FIG. 5 is a schematic diagram of a device of laser differential confocal mapping-spectrum microscopic imaging with a non-confocal spectrum detection system.

The device in FIG. 5 is configured by replacing the spectrum detection system 22 as shown in FIG. 4 with a general spectrum system comprising a seventh converging lens 46, a second spectrometer 47 and a fifth detector 48.

Figure 6:
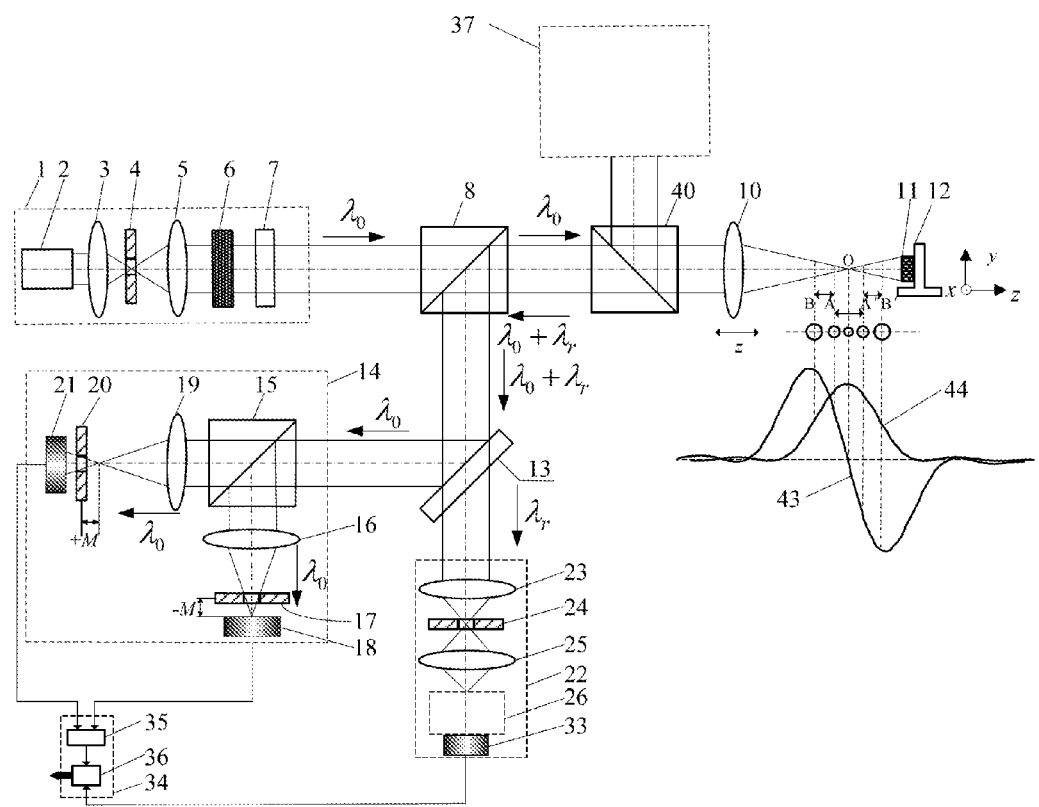
FIG. 6 is a schematic diagram of a device of laser differential confocal mapping-spectrum microscopic imaging with the microscopic function.

The device in FIG. 6 is configured by adding a fourth beam splitting system 40 between the first beam splitting system 8 and the objective 10 and adding a microscopic observation system 37 in the reflection direction of the fourth beam splitting system 40 in the device as shown in FIG. 4.

Figure 7:
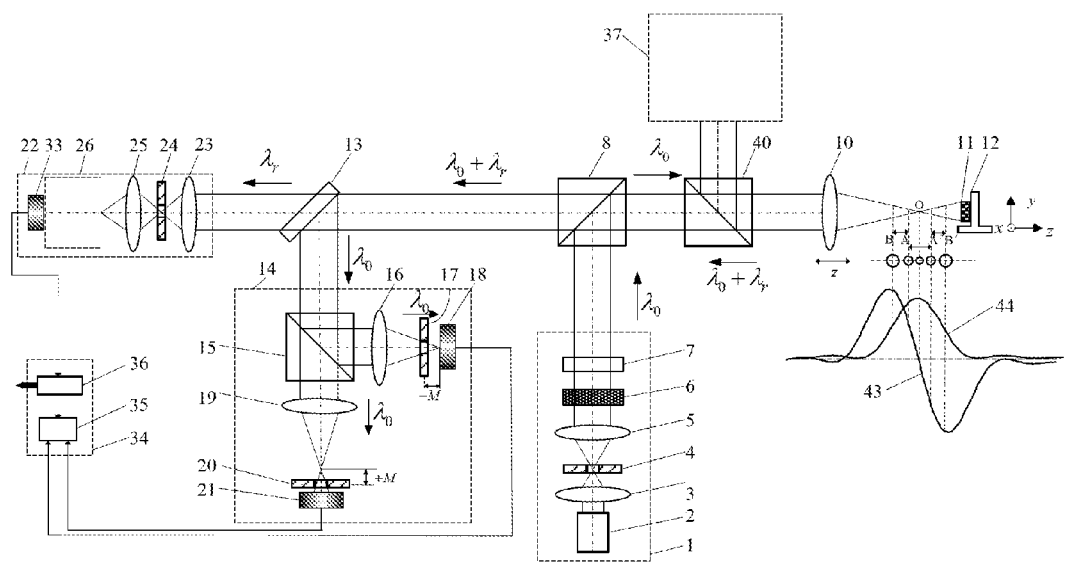
FIG. 7 is a schematic diagram of a device of reflection-type laser differential confocal mapping-spectrum microscopic imaging with the microscopic function.

The device in FIG. 7 is configured by placing the excitation beam generation system 1 as shown in FIG. 6 in the reflection direction of the first beam splitting system 8 and placing the dichroic beam splitting system 13 in the transmission direction of the first beam splitting system 8.

In this embodiment, the polarization modulator 6 may be a radially polarized light generator, the first beam splitting system 8 may be a non-polarizing beam splitter, the second beam splitting system 15 may be a non-polarizing beam splitter, the third beam splitting system 39 may be a broadband beam splitter, the fourth beam splitting system 40 may be a non-polarizing beam splitter, the dichroic beam splitting system 13 may be a Notch filter and the spectrum detection system 22 may be a Raman spectrum detection system.

Figure 8:
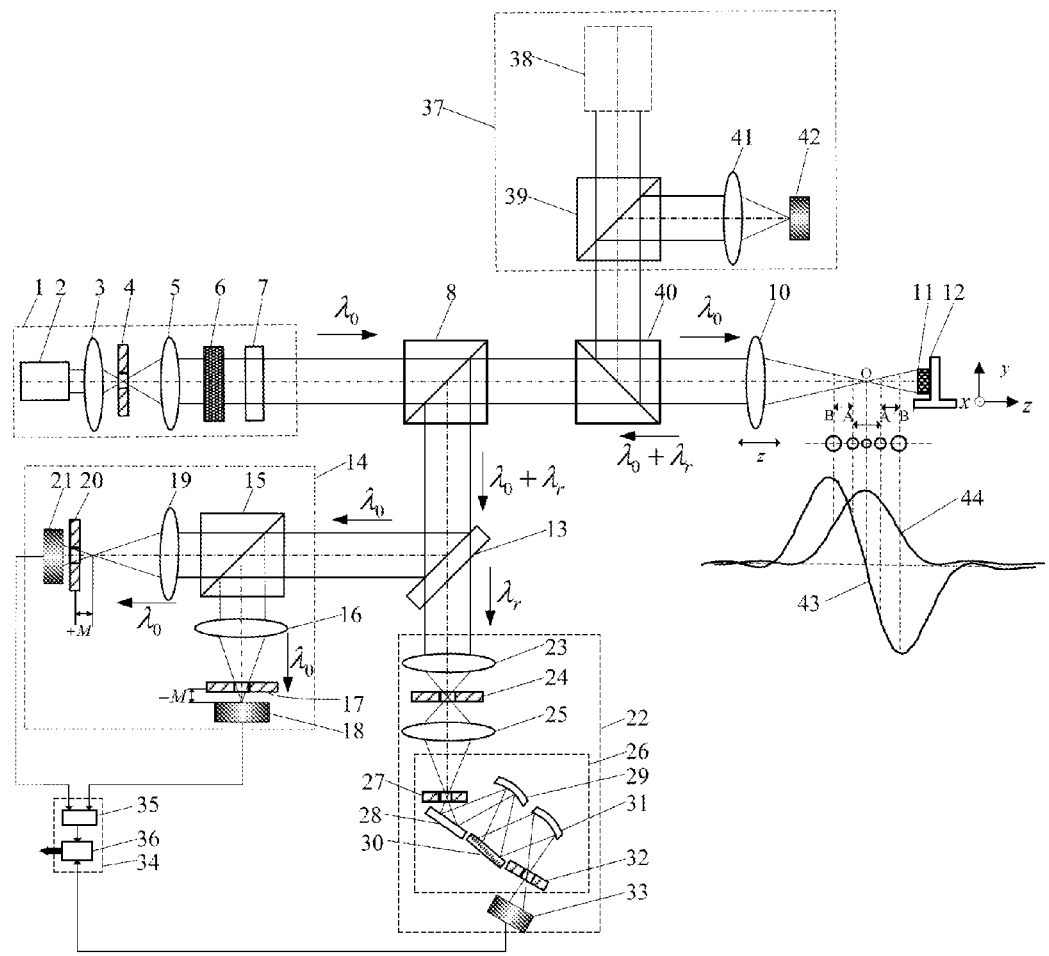
FIG. 8 is a diagram of an embodiment of laser differential confocal mapping-spectrum microscopic imaging method and device.

As shown in FIG. 8, the test steps of laser differential confocal mapping-spectrum microscopic imaging method are as follows:

At first, a kohler illumination system 38 may generate uniform white light. After passing through the broadband beam splitter 39, the white light may be reflected by the non-polarizing beam splitter 40 and focus on the measured sample 11 via the objective 10. The white light then may be reflected into the original light path, pass through the objective 10, and be reflected by the non-polarizing beam splitter 40 and the broadband beam splitter 39, respectively. Sequentially, after passing through a sixth converging lens 41, the white light may enter into a fourth detector 42. By viewing the image in the fourth detector 42 to observe the measured sample 11, so as to determine the area required to view of the measured sample 11 to perform the position of the measured sample 11 roughly.

Then, the beam emitted from a laser 2 may be collimated and expanded to parallel light via a first converging lens 3, a first pinhole 4 and an eighth converging lens 5. The beam may become radially polarized light via a radially polarized light generator 6. The radially polarized light may be modulated via a pupil filter 7. After transmitting through the non-polarizing beam splitter 8 and the objective 10, the converging spot is compressed and focused on the measured sample 11, and excite Rayleigh light and Raman scattering light that carries the spectral characteristics of the measured sample 11. The measured sample 11 may be processed through Raman enhancing technology such as the nanoparticles to increase the intensity of the Raman scattering light.

The measured sample 11 may be moved, so that the Rayleigh light and the Raman scattering light corresponding to different areas of the measured sample 11 may be collected into the original light path by the system, and may be reflected into the detecting part by the non-polarizing beam splitter 8 after passing through the objective 10 and transmitting through the non-polarizing beam splitter 40. In this case, the Raman scattering light may transmit through the Notch filter 13 into the Raman spectrum detection system 22. The Raman spectrum detection system 22 may be a confocal Raman spectrum detection system. The Raman scattering light may be focused on a fourth pinhole 24 via a fourth converging lens 23 and focused onto a first spectrometer 26 via a fifth converging lens 25. The Raman scattering light may pass through an incident slit 27 and reflected by a planar reflector 28 and a first concave reflective converging lens 29 into a spectrum grating 30. The light diffracted via the spectrum grating 30 may be reflected by a second concave reflective converging lens 31 to focus on an exit slit 32 and then enter into a third detector 33. Due to the diffraction of the grating, the lights with different wavelengths in the Raman spectrum may be separated from each other. Therefore, the light emitted from the exit slit 32 is monochromatic light. When the spectrum grating 30 is rotated, the lights emitted from the exit slit 32 may have different wavelengths. The Raman spectrum of the measured sample 11 may be obtained by observing the response value of the third detector 33 and the rotational angle of the grating. The Rayleigh light may be reflected into the differential confocal detection system 14 by the Notch filter 13. The Rayleigh light may be divided into two beams by a non-polarizing beam splitter 15. The portion of the Rayleigh light reflected by the non-polarizing beam splitter 15 may be focused by a second converging lens 16, and then received by a first detector 18 which is behind a second pinhole 17 after penetrating through the second pinhole 17 which is in front of the focus of the second converging lens 16 with a distance of M. The portion of the Rayleigh light transmitted by the non-polarizing beam splitter 15 may be focused by a third converging lens 19, and then received by a second detector 21 which is behind a third pinhole 20 after penetrating through a third pinhole 20 which is behind the focus of the third converging lens 19 with a distance of M.

In the process of measurement, when the measured sample 11 is axially and laterally scanned, intensity responses which reflect the height of the measured sample 11 and which are detected by the two detectors, namely, a second detector 21 and the first detector 18, in the differential confocal detection system 14, respectively, may be $I_1(v, u, +u_M)$ and $I_2(v, u, -u_M)$. The obtained intensity responses of $I_1(v, u, +u_M)$ and $I_2(v, u, -u_M)$ may be transmitted to a differential subtraction module 35 to perform a process of differential subtraction and work out a differential confocal intensity responses of $I(v, u, u_M)$:

$$I(v,u,u_M) = I_1(v,u,+u_M) - I_2(v,u,-u_M) \quad \text{Formula (1)}$$

In above focusing theory, the focusing only concerns the response in the axial direction (namely z-axial direction in the figures), regardless of the response in the lateral direction (namely x-axial direction and y-axial direction in the figures). Therefore, the scanning represented in Formula (1) refers to an axial scanning substantially.

Accordingly, the microscopic chromatography imaging of geometric position of the measured sample 11 may be achieved. In Formula (1), v is lateral normalized optical coordinate, u is axial normalized optical coordinate, and $u_M$ is the axial normalized offset of a pinhole.

The spectrum signal of Raman scattering light which is detected by the third detector 33 in the spectrum detection system 22 and which carries the spectral information of the measured sample 11 may be $I(\lambda)$ (wherein, $\lambda$ is wavelength).

$I(\lambda)$ and $I(v,u,u_M)$ may be transmitted to a data fusion module 36 for data processing so as to obtain a four dimensional measurement information $I(v, u, \lambda)$ which includes the position information $I(v, u, u_M)$ and the spectral information $I(\lambda)$ of the measured sample 11.

The measured sample 11 may be scanned in the x-axial and y-axial directions and the objective 10 may be scanned in the z-axial direction. Above steps are repeated so as to obtain a set of i pieces of sequence measurement information $\{I_i(\lambda), I_i(v, u)\}$ which include the position information $I(v, u, u_M)$ and the spectral information $I(\lambda)$ corresponding to the near focus of the objective.

The position information $I_i(v, u, u_M)$ corresponding to a distinguishable area $\delta_i$ may be used to obtain the value of the spectral information $I_i(\lambda)$ corresponding to the area $\delta_i$. Then, according to the relation between v and lateral position coordinates (x, y) and the relation between u and axial position coordinates (z), the information $I_i(x_i, y_i, z_i, \lambda_i)$ reflecting the three dimensional size and the spectral characteristics of the micro-area $\delta_i$ of the measured sample 11 may be reconstituted.

The three dimensional size and the spectral characteristics corresponding to a distinguishable minimum area $\delta_{min}$ may be determined by a formula (2):

$$I_{\sigma_{min}}(x,y,z,\lambda) = I_i(x,y,z,\lambda)|_{I_i(v,u)=0, I_1(v,u,+u_M)=0, I_2(v,u,-u_M)=0} \quad \text{Formula (2)}$$

Accordingly, a nano-scale micro-area laser differential confocal mapping-spectrum microscopic imaging may be achieved.

Meanwhile, different measurement values $\{z_i\}$ in BB' section of the differential confocal axial response curve may be used to obtain the spectral characteristics $I_{\delta i}(z_i, \lambda_i)$ corresponding to the positions of different measurement values. Accordingly, a micro-area controllable spectral characteristics test in the vicinity of the excitation focus may be accomplished.

As it could be seen from FIG. 8, the focus of excitation spot may be accurately captured through the absolute zero O of the differential confocal detection system 14, and the spectrum detection and three dimensional geometric position detection of a minimum area $\delta_{min}$ may be accomplished by extracting the excitation spectrum corresponding to the focus O from the sequence measurement data $\{I_i(\lambda), I_i(v, u)\}$.

$$I_{\sigma_{min}}(x, y, z, \lambda) = \begin{cases} I_i(x, y, z, \lambda)|_{I_i(v,u)=0, I_1(v,u,+u_M) \neq 0, I_2(v,u,-u_M) \neq 0} & \text{Micro-area mapping-spectrum chromatography imaging} \\ I_i(x, y, z) & \text{Three-dimensional chromatography imaging} \\ I_i(\lambda) & \text{Spectral test} \end{cases} \quad \text{Formula (3)}$$

Three measurement modes, namely, micro-area mapping-spectrum chromatography imaging, three-dimensional chromatography and spectral test, represented in formula (3) may be accomplished by fusing the measurement information $\{I_i(\lambda), I_i(v, u)\}$.

As shown in FIG. 8, the laser differential confocal mapping-spectrum microscopic imaging device may include, sequentially placed along the light path, the excitation beam generation system 1, the non-polarizing beam splitter 8, the objective 10, the measured sample 11, and the 3D scanning stage 12 which are positioned in the emission direction of the excitation beam generation system 1, the Notch filter 13 positioned in the reflection direction of the non-polarizing beam splitter 8, the Raman spectrum detection system 22 positioned in the transmission direction of the Notch filter 13, the differential confocal detection system 14 positioned in the reflection direction of the Notch filter 13, and the data processing module 34 positioned in the joint of the differential confocal detection system 14 and the Raman spectrum detection system 22. In the above, the excitation beam generation system 1 may be used to generate the excitation beam, and may include, sequentially placed along the light path, the laser 2, the first converging lens 3, the first pinhole 4 positioned at the focus of the first converging lens 3, the eighth converging lens 5, the radially polarized light generator 6 and the pupil filter 7. The Raman spectrum detection system 22 may include, sequentially placed along the light path, the fourth converging lens 23, the fourth pinhole 24 positioned at the focus of the fourth pinhole 24, the fifth converging lens 25 behind the fourth pinhole 24, the first spectrometer 26 positioned at the focus of the fifth converging lens 25, and the third detector 33 behind the first spectrometer 26. The first spectrometer 26 may include, sequentially placed along the light path, the incident slit 27, the planar reflector 28, the first concave reflective converging lens 29, the spectrum grating 30, the second concave reflective converging lens 31 and the exit slit 32. The differential confocal detection system 14 may include, sequentially placed along the light path, the non-polarizing beam splitter 15, the third converging lens 19 positioned in the transmission direction of the non-polarizing beam splitter 15, the third pinhole 20, the second detector 21, the second converging lens 16 positioned in the reflection direction of the non-polarizing beam splitter 15, the second pinhole 17 and the first detector 18. The third pinhole 20 is positioned behind the focus of the third converging lens 19 with a distance of M, and the second pinhole 17 is positioned in front of the focus of the second converging lens 16 with a distance of M. The data processing module 34 may include the differential subtraction module 35 and the data fusion module 36 for the fusion processing of the sampled data.

The testing steps according to the present invention will be further described in connection with the embodiment as shown in FIG. 8.

At step 110, as described above, the measured sample 11 may be observed by the microscopic observation system 37.

At step 120, the beam emitted from the laser 2 may be collimated and expanded to parallel light via the first converging lens 3, the first pinhole 4 and the eighth converging lens 5, it may become radially polarized light via the radially polarized light generator 6, the radially polarized light may be modulated via a pupil filter 7, after transmitting through the non-polarizing beam splitter 8, and the objective 10, the converging spot is compressed and focused on the measured sample 11, and excite Rayleigh light and Raman scattering light that carries the spectral characteristics of the measured sample 11, and the measured sample 11 may be processed through Raman enhancing technology such as the nanoparticles to increase the intensity of the Raman scattering light.

At step 130, the 3D scanning stage 12 or the objective 10 may be axially moved to axial scan the measured sample 11; when it is moved, the Rayleigh light and the Raman scattering light corresponding to different areas of the measured sample 11 may be collected into the original light path by the system, and may be reflected into the detecting part by the non-polarizing beam splitter 8 after passing through the objective 10 and transmitting through the non-polarizing beam splitter 40. In the above, the Raman scattering light may transmit through the Notch filter 13 into the Raman spectrum detection system 22, wherein the Raman spectrum detection system 22 may be a confocal Raman spectrum detection system; the Rayleigh light may be reflected into the differential confocal detection system 14 by the Notch filter 13.

In the above, the operation of the Raman spectrum detection system 22 and the differential confocal detection system 14 may be substantially the same as described above and the explanation thereof will be omitted.

In the process of measurement, when the measured sample 11 is scanned in the axial direction (in the z-axial direction in the FIG. 8), intensity responses which reflect the height of the measured sample 11 and which are detected by the two detectors, namely, the second detector 21 and the first detector 18, in the differential confocal detection system 14, respectively, may be $I_1(v, u, +u_M)$ and $I_2(v, u, -u_M)$. The obtained intensity responses of $I_1(v, u, +u_M)$ and $I_2(v, u, -u_M)$ may be transmitted to a differential subtraction module 35 to perform a process of differential subtraction and work out a differential confocal intensity responses of $I(v, u, u_M)$:

$$I(v,u,u_M)=I_1(v,u,+u_M)-I_2(v,u,-u_M) \quad \text{Formula (1)}$$

In Formula (1), v is lateral normalized optical coordinate, u is axial normalized optical coordinate, and $u_M$ is the axial normalized offset of a pinhole.

In above focusing theory, the focusing only concerns the response in the axial direction (namely z-axial direction in the drawings), regardless of the response in the lateral direction (namely x-axial direction and y-axial direction in the drawings). Therefore, the scanning represented in Formula (1) refers to an axial scanning substantially.

A differential confocal curve 43 may be completed by fitting according to the result of the Formula (1). The focus O of the objective 10 may be obtained by using the property that the zero-cross point of the differential confocal curve corresponds to the focus of the objective, and the measured sample 11 may be moved to the focus O by the 3D scanning stage 12 (or the movement of the objective 10). At this time, the Raman scattering light of the measured sample 11 at the focus O may be recaptured.

The Raman spectrum detection system 22 may be used to gather spectrum of the measured sample 11 at the focus O. The spectrum signal of Raman scattering light which is detected by the third detector 33 and which carries the spectral information of the measured sample 11 may be $I(\lambda)$ (wherein, $\lambda$ is wavelength).

$I(\lambda)$ and $I(v,u,u_M)$ may be transmitted to the data fusion module 36 for data processing so as to obtain a four dimensional measurement information $I(v, u, \lambda)$ which includes the position information $I(v, u, u_M)$ and the spectral information $I(\lambda)$ of the measured sample 11.

As to the sample micro-area $\delta_j$ of the measured sample 11 corresponding to the focus O, further according to the relation between v and lateral position coordinates (x, y) and the relation between u and axial position coordinates (z), the information $I_i(x, y, z, \lambda)$ reflecting the three dimensional size and the spectral characteristics of the sample micro-area $\delta_j$ of the measured sample 11 corresponding to the focus O may be reconstituted.

The information $I_i(x, y, z, \lambda)$ of the three dimensional size and the spectral characteristics of the sample micro-area $\delta_j$ of the measured sample 11 may be determined by Formula (4):

$$I_{\sigma_j}(x,y,z,\lambda)=I_i(x,y,z,\lambda)|_{I_i(v,u)=0, I_1(v,u,+u_M)=0, I_2(v,u,-u_M)=0} \quad \text{Formula (4)}$$

Accordingly, a nano-scale micro-area laser differential confocal mapping-spectrum microscopic imaging may be achieved.

Upon above steps, the measured sample 11 may be laterally (namely, in the x-axial and y-axial directions in the figures) scanned by using the 3D scanning stage 12. After being moved to next stop, the measured sample 11 may be axially (namely, in the z-axial direction in the figures) scanned by using the 3D scanning stage 12 (or the objective driver in the objective). After having the focus O of the objective 10, the measured sample 11 may be moved to the focus O to obtain the spectral information.

The accurate spectral information may be obtained and the spectrum detection and three dimensional geometric position detection at focus accomplished through above processes. In this case, three measurement modes, namely, micro-area mapping-spectrum chromatography imaging, three-dimensional chromatography imaging and spectral test, represented in formula (5) may be accomplished by the fusion process of the measurement information $\{I_i(\lambda), I_i(v, u)\}$.

$$I_{\sigma_j}(x, y, z, \lambda) = \begin{cases} I_i(x, y, z, \lambda)|_{I_i(v,u)=0, I_1(v,u,+u_M)\neq 0, I_2(v,u,-u_M)\neq 0} & \text{Micro-area mapping–spectrum chromatography imaging} \\ I_i(x, y, z) & \text{Three-dimensional chromatography imaging} \\ I_i(\lambda) & \text{Spectral test} \end{cases} \quad \text{Formula (5)}$$

In addition, in the present invention, the step 130 may further comprise:

When the 3D scanning stage 12 or the objective 10 is moved, the Rayleigh light (a set of which is used to obtain the differential confocal curve) of the measured sample 11 may be captured. Then, during the axial scanning of the measured sample 11, except for the differential confocal curve, a set of i pieces of sequence measurement information $\{I_i(\lambda), I_i(v, u)\}$ which include the position information $I(v, u, u_M)$ and the spectral information $I(\lambda)$ corresponding to the near focus O of the objective may be obtained; each i corresponds to a distinguishable area $\delta_i$ irradiated by one light spot during the axial scanning.

The position information $I_i(v, u, u_M)$ corresponding to the distinguishable area $\delta_i$ may be used to obtain the value of the spectral information $I_i(\lambda)$ corresponding to the area $\delta_i$. Further, according to the relation between v and lateral position coordinates (x, y) and the relation between u and axial position coordinates (z), the information $I_i(x_i, y_i, z_i, \lambda_i)$ reflecting the three dimensional size and the spectral characteristics of the micro-area $\delta_i$ of the measured sample 11 may be reconstituted.

The three dimensional size and the spectral characteristics corresponding to a distinguishable minimum area $\delta_{min}$ may be determined by a formula (2):

$$I_{\sigma_{min}}(x,y,z,\lambda)=I_i(x,y,z,\lambda)|_{I_i(v,u)=0, I_1(v,u,+u_M)=0, I_2(v,u,-u_M)=0} \quad \text{Formula (2)}$$

Accordingly, a nano-scale micro-area laser differential confocal mapping-spectrum microscopic imaging may be achieved. The distinguishable minimum area $\delta_{min}$ may be an area corresponding to the focus O.

Additionally, during above processes, different measurement values $\{z_i\}$ in BB' section of the differential confocal axial response curve may be used to obtain the spectral characteristics $I_{\delta i}(z_i, \lambda_i)$ corresponding to the positions of different measurement values. Accordingly, a micro-area controllable spectral characteristics test in the vicinity of the excitation focus may be accomplished.

As described above, it could be seen from FIG. 8, the focus of excitation spot may be accurately captured through the absolute zero O of the differential confocal detection system 14, and the spectrum detection and three dimensional geometric position detection of the minimum area $\delta_{min}$ may be accomplished by extracting the excitation spectrum corresponding to the focus O from the sequence measurement data $\{I_i(\lambda), I_i(v, u)\}$.

$$I_{\sigma_{min}}(x, y, z, \lambda) = \begin{cases} I_i(x, y, z, \lambda)|_{I_i(v,u)=0, I_1(v,u,+u_M)\neq 0, I_2(v,u,-u_M)\neq 0} & \\ I_i(x, y, z) & \text{Three-dimensional chromatography imaging} \\ I_i(\lambda) & \text{Spectral test} \end{cases} \quad \text{Formula (3)}$$

Three measurement modes, namely, micro-area mapping-spectrum chromatography imaging, three-dimensional chromatography imaging and spectral test, represented in formula (3) may be accomplished by the fusion process of the measurement information $\{I_i(\lambda), I_i(v, u)\}$.

The various embodiments in the description have been explained step by step. Any one of the embodiments has only emphasized the differences from others, and the same or similar explanations between embodiments could be made reference to each other.

It will be understood that, although the terms "first", "second", etc. are only used to distinguish one element or operation from another one, and does not necessarily require or suggest that there are any actual relationship or order between these elements or operations. Further, the terms "comprise", "include" and any other variants thereof are intended to cover a non-exclusive "comprise", so that process, method, product or equipment which includes a series of elements may include not only those elements, but also other elements that do not be definitely listed, or also may include the inherent elements of the process, method, product or equipment. In the absence of more restrictions, an element defined by the statement "includes a/an . . . " does not mean to exclude other same elements in the process, method, product or equipment including this element.

The laser differential confocal mapping-spectrum microscopic imaging method and device provided in the present invention has been described in detail above. Herein, the principle and implement of the present invention has explained by way of specific examples. Above description of the embodiments is only used to facilitate the understanding of the method and main concept of the present invention. Meanwhile, modifications could be made by an ordinary person skilled in the art according to the concept of the present invention within the scope of the specific embodiments and their applications. In conclusion, the description of the present invention should not be constructed as a limit to the present invention.

The invention claimed is:

1. A laser differential confocal mapping-spectrum microscopic imaging method, comprising:
   a) after passing through a first beam splitting system and an objective, excitation beam generated by an excitation beam generation system being focused on a measured sample and excited Rayleigh light and Raman scattering light that carries the spectral characteristics of the measured sample, the excited Raman scattering light and the Rayleigh light being recycled to the light path by a system and then be reflected to a dichroic beam splitting system by a first beam splitting system after passing through the objective, after being split by the dichroic beam splitting system, the Raman scattering light and the Rayleigh light being separated from each other, the Rayleigh light being reflected into a differential confocal detection system, while the Raman scattering light being transmitted into a spectrum detection system, and based on the property that the zero-cross point of the differential confocal curve accurately corresponds to the focus of the objective, accurately-captured spectral information of the focus of the excitation spot being positioned by a zero triggering technology to accomplish spectrum detection with high spatial resolution;
   b) when a differential subtraction process is made only to the signal of the received Rayleigh light, a laser differential confocal mapping-spectrum microscopic imaging device performs a three-dimensional chromatography imaging with high spatial resolution; when a process is made only to the spectrum signal of the received Raman scattering light, the laser differential confocal mapping-spectrum microscopic imaging device performs a spectrum detection; when a process is made to the signals of both the received Rayleigh light and the Raman scattering light, the laser differential confocal mapping-spectrum microscopic imaging device performs a micro-area mapping-spectrum chromatography imaging with high spatial resolution that is a "mapping & spectrum in one" with high spatial resolution of geometric position information and spectral information of the measured sample;
   c) the zero-cross point of the differential confocal curve accurately corresponding to the focus of the objective, so that in the measurement process, the measured sample being accurately and real-time focus-tracked to ensure the measured sample to always be focused during the whole measurement process, thereby restraining the influence of the factors such as environment temperature and vibration on the spectral measurement so as to improve the accuracy of measurement;
   d) the zero-cross point of the differential confocal curve corresponding to the focus of the measurement objective at which the converging spot and detection area have the smallest size, other position in a linear section corresponding to the out-of-focus area of the objective, and the size of the converging spot in front of or behind the focus within the liner section increasing as the out-of-focus amount increases, in such a manner that the size of the converging spot is controlled by adjusting z-axial out-of-focus amount of the sample and according to the requirement of actual measurement accuracy, thus allowing the size of the detection area of the sample to be controllable.

2. The laser differential confocal mapping-spectrum microscopic imaging method according to claim 1, wherein the excitation beam is a polarized beam that comprises linearly polarized light, circularly polarized light or radially polarized light; or the excitation beam is a structural beam generated by a pupil filtering process, when used with the pupil filtering process, it is able to compress the size of the measuring converging spot to improve the lateral resolution of the system.

3. The laser differential confocal mapping-spectrum microscopic imaging method according to claim 1, wherein the system is further used to detect the scattering spectrum which includes scattering spectrums of detection fluorescence, brillouin scattering light and Compton scattering light.

4. A laser differential confocal mapping-spectrum microscopic imaging device, comprising:
   an excitation beam generation system, a first beam splitting system, an objective, a 3D scanning stage, a dichroic beam splitting system, a spectrum detection system, a differential confocal detection system and a data processing module; a measured sample is placed on the 3D scanning stage;
   wherein the first beam splitting system, the objective and the 3D scanning stage are sequentially placed in the emission direction of the excitation beam generation system, the dichroic beam splitting system is positioned in the reflection direction of the first beam splitting system, the first beam splitting system reflects the light signal excited from the surface of the measured sample to the dichroic beam splitting system; the spectrum detection system is positioned in the transmission direction of the dichroic beam splitting system, the differential confocal detection system is positioned in the reflection direction of the dichroic beam splitting system, and the data processing module is connected to the spectrum detection system and the differential confocal detection system; wherein the data processing module comprises a differential subtraction module and a data fusion module; the data processing module processes the information obtained by the spectrum detection system and the differential confocal detection system synchronously and in real time; or, the excitation beam generation system is placed in the reflection direction of the first beam splitting system, the dichroic beam splitting system is sequentially placed in the transmission direction of the first beam splitting system along the light path, the spectrum detection system is positioned in the transmission direction of the dichroic beam splitting system, the differential confocal detection system is positioned in the reflection direction of the dichroic beam splitting system, the data processing module is connected to the differential confocal detection system and the spectrum detection system;
   wherein the data processing module comprises a differential subtraction module and a data fusion module; the data processing module processes the information obtained by the spectrum detection system and the differential confocal detection system synchronously and in real time; and
   wherein a Raman scattering light and a Rayleigh light are separated from each other by the dichroic beam splitting system; the Rayleigh light being reflected into the differential confocal detection system, while the Raman scattering light is being transmitted into a spectrum detection system.

5. The laser differential confocal mapping-spectrum microscopic imaging device according to claim 4, wherein the spectrum detection system is a general spectrum detection system, which includes, sequentially placed along the light path, a converging lens, a spectrometer positioned at the focus of the converging lens, and a detector positioned behind the spectrometer; wherein the general spectrum detection system performs a spectrum detection of a surface layer of the measured sample;

or, the spectrum detection system is a confocal spectrum detection system, which includes, sequentially placed along the light path, a converging lens, a pinhole positioned at the focus of the converging lens, a second converging lens positioned behind the pinhole, a first spectrometer positioned at the focus of the second converging lens, and a detector positioned behind the first spectrometer; wherein the confocal spectrum detection system performs a spectrum chromatography detection of the measured sample.

6. The laser differential confocal mapping-spectrum microscopic imaging device according to claim 4, wherein the excitation beam generation system further includes a polarization modulator and a pupil filter; wherein the polarization modulator is configured to generate a polarized light, and the pupil filter is configured to generate a structural beam.

7. The laser differential confocal mapping-spectrum microscopic imaging device according to claim 6, wherein the pupil filter configured to compress the excitation spot is placed between the polarization modulator and the first beam splitting system, or is placed between the first beam splitting system and the objective.

8. The laser differential confocal mapping-spectrum microscopic imaging device according to claim 4, wherein the device further includes a second beam splitting system and a microscopic observation system positioned in the reflection direction of the second beam splitting system; wherein the microscopic observation system further comprises a kohler illumination system, a third converging lens, a third beam splitting system and a second detector; wherein the second beam splitting system is positioned between the excitation beam generation system and the first beam splitting system or is positioned between the first beam splitting system and the objective.

9. The laser differential confocal mapping-spectrum microscopic imaging device according to claim 4, wherein the data processing module includes a differential subtraction module configured to process the position information, and a data fusion module configured to fuse the position information and the spectral information.

10. A laser differential confocal mapping-spectrum microscopic imaging method, comprising:
during a lateral scanning of a measured sample, real-timely aiming to each of determined scanning points, a focus of an objective being accurately tracked utilizing a set of axially detected differential confocal intensity response signals; after the focalization, based on the property that a zero-cross point of the differential confocal curve accurately corresponding to the focus of the objective, the spectral information at the focus of the excitation spot being accurately captured by the zero trigger;
wherein the differential confocal signal and the spectral information are obtained by the following steps:
an excitation beam generation system generating an excitation beam,
after passing through a first beam splitting system and an objective placed sequentially, the excitation beam focusing on the measured sample and exciting, a Rayleigh light and Raman scattering light that carries the spectral characteristics of the measured sample; the Rayleigh light and the Raman scattering light being recycled into the light path by a system, follow the passage of the objective and the first beam splitting system, then entering a dichroic beam splitting system to split the light, the Rayleigh light being reflected into a differential confocal detection system and the differential confocal intensity response signal carrying geometric position information of the measured sample being obtained via the differential confocal detection system, while the Raman scattering light being transmitted into a spectrum detection system and the spectrum signals carrying the spectral characteristics of the measured sample being obtained via the spectrum detection system;

after each of the scanning points in the lateral direction of the measured sample being real-time focus-tracked according to the above steps and then spectrum signals of the scanning points being accurately captured, a set of differential confocal signals carrying the geometric position information of the measured sample and spectrum signals carrying the spectral characteristics of the measured sample being obtained, the signals being transmitted to a data processing module to be processed; wherein the processing includes: when the differential confocal signals being only processed, the system performs a three-dimensional chromatography imaging with high spatial resolution; or when the spectrum signals being only processed, the system performs a spectrum detection; or when both the differential confocal signals and the spectrum signals are processed, the system performs a micro-area mapping-spectrum chromatography imaging with high spatial resolution; wherein the micro-area mapping-spectrum chromatography imaging is a "mapping & spectrum in one" with high spatial resolution in which the geometric position information and spectral information of the measured sample are detected simultaneously;

wherein during the accurate capture of the spectrum signals, the method further includes: by means of the differential confocal curve, the size of the converging spot being controlled by adjusting an axial out-of-focus amount of the sample and according to the requirement of actual measurement accuracy.

11. The laser differential confocal mapping-spectrum microscopic imaging method according to claim 10, wherein the step of real-time focus-tracking and accurately capturing the spectrum signals of each of the determined scanning points according to a set of axially detected differential confocal intensity response signals, comprising:
axial scanning being performed at lateral planar positions where the scanning points are located to obtain a set of differential confocal intensity response signals, then the differential confocal intensity response signals being transmitted to the data processing system, the data processing system fitting the differential confocal intensity response signals into the differential confocal curve and the focus of the objective being determined according to the differential confocal curve.

12. The laser differential confocal mapping-spectrum microscopic imaging method according to claim 11, wherein the step of, after the focalization, based on the property that the zero-cross point of the differential confocal curve accurately corresponding to the focus of the objective, the spectral information at the focus of the excitation spot being accurately captured by the zero trigger, comprising:
the objective or the measured sample being axially moved according to the focus of the focalized objective, to make the measured sample be positioned at the focus of the objective;
the Raman scattering light of the measured sample in focus being captured and recycled to the light path, and the spectrum signal that carries the spectral characteristics of the measured sample being obtained by the spectrum detection system.

13. The laser differential confocal mapping-spectrum microscopic imaging method according to claim 10, wherein the step of, after the focalization, based on the property that the zero-cross point of the differential confocal curve accurately corresponding to the focus of the objective, the spectral information at the focus of the excitation spot being accurately captured by the zero trigger, comprising:

the objective or the measured sample being axially moved according to the focus of the focalized objective, to make the measured sample be positioned at the focus of the objective;

the Raman scattering light of the measured sample in focus being captured and recycled to the light path, and the spectrum signal that carries the spectral characteristics of the measured sample being obtained by the spectrum detection system.

14. The laser differential confocal mapping-spectrum microscopic imaging method according to claim 10, wherein the step of controlling the size of the converging spot according to the requirement of actual measurement accuracy by means of the differential confocal curve, and by adjusting an axial out-of-focus amount of the sample, comprising:

according to a characteristic that the non-focal position in the linear section BB' of the differential confocal curve corresponds to the out-of focus area of the objective and the size of the converging spot in front of or behind the focus within the section BB' increases as the out-of-focus amount increases; by mean of the differential confocal curve, the size of the converging spot being controlled by adjusting the axial out-of-focus amount of the sample and according to the requirement of actual measurement accuracy, thus allowing the size of the detection area of the sample to be controllable.

15. The laser differential confocal mapping-spectrum microscopic imaging method according to claim 10, wherein the excitation beam is a polarized beam, wherein the type of the polarized beam comprises: linearly polarized light, circularly polarized light or radially polarized light; or the excitation beam is a structural beam generated by a pupil filtering process, wherein the structural beam generated by the pupil filtering process is used to compress the size of the measuring converging spot to improve the lateral resolution of the system.

16. The laser differential confocal mapping-spectrum microscopic imaging method according to claim 10, wherein the method further is able to detect the scattering spectrum, wherein the scattering spectrum includes the scattering spectrums of fluorescence, brillouin scattering light and Compton scattering light.

* * * * *